United States Patent
Areste et al.

(10) Patent No.: US 8,681,942 B2
(45) Date of Patent: Mar. 25, 2014

(54) FLUOROSCOPY SYSTEMS AND METHODS (75) Inventors: Romain Xavier Areste, Milwaukee, WI (US); Vivek Walimbe, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 526 days.

(21) Appl. No.: 12/986,673

(22) Filed: Jan. 7, 2011

(65) Prior Publication Data
US 2012/0177178 A1 Jul. 12, 2012

(51) Int. Cl.
H05G 1/56 (2006.01)
H05G 1/58 (2006.01)
H05G 1/08 (2006.01)

(52) U.S. Cl.
USPC ............ 378/114; 378/42; 378/91; 378/115; 378/116

(58) Field of Classification Search
USPC ......... 378/41, 42, 91, 98, 114–116, 145, 204, 378/210, 901
See application file for complete search history.

(56) References Cited

U.S. PATENT DOCUMENTS

| 6,178,228 | B1 * | 1/2001 | Schol ............................ 378/162 |
| 6,285,741 | B1 * | 9/2001 | Ackelsberg et al. .......... 378/110 |
| 6,375,354 | B1 | 4/2002 | Polkus et al. |
| 6,402,373 | B1 | 6/2002 | Polkus et al. |
| 6,422,749 | B1 | 7/2002 | Polkus et al. |
| 6,435,716 | B1 | 8/2002 | Polkus et al. |
| 6,987,834 | B2 | 1/2006 | Omernick et al. |
| 7,261,465 | B2 | 8/2007 | Butzine et al. |
| 7,298,825 | B2 | 11/2007 | Omernick et al. |
| 7,324,628 | B2 | 1/2008 | Liu et al. |
| 7,720,523 | B2 | 5/2010 | Omernick et al. |
| 8,041,093 | B2 | 10/2011 | Omernick et al. |
| 2006/0072700 | A1 * | 4/2006 | Chen et al. ........................ 378/4 |
| 2006/0242268 | A1 | 10/2006 | Omernick et al. |
| 2007/0273697 | A1 | 11/2007 | Zaman et al. |
| 2008/0232548 | A1 | 9/2008 | Tanaka |
| 2008/0319275 | A1 | 12/2008 | Chiu |
| 2010/0061507 | A1 | 3/2010 | Fujii |
| 2010/0082294 | A1 * | 4/2010 | Adnani ........................ 702/182 |
| 2010/0128955 | A1 | 5/2010 | Walimbe et al. |
| 2010/0231573 | A1 * | 9/2010 | Adachi ........................ 345/211 |
| 2011/0051902 | A1 | 3/2011 | Liu et al. |
| 2011/0255666 | A1 | 10/2011 | Liu et al. |
| 2011/0274251 | A1 | 11/2011 | Omernick et al. |
| 2011/0286575 | A1 | 11/2011 | Omernick et al. |
| 2012/0002853 | A1 | 1/2012 | Omernick et al. |

FOREIGN PATENT DOCUMENTS

WO 2005041775 A1 5/2005
WO 2008096688 A1 8/2008

* cited by examiner

*Primary Examiner* — Anastasia Midkiff
(74) *Attorney, Agent, or Firm* — Fletcher Yoder, P.C.

(57) ABSTRACT

Fluoroscopy imaging systems including an X-ray generator, a detector, and control circuitry coupled to the detector are provided. The control circuitry may be adapted to receive a digital signal from the detector, to process the digital signal, and to communicate the processed digital signal to a monitor for display during a fluoroscopy imaging operation. The fluoroscopy imaging systems may also include a user interface having at least one configurable adjustment configured to enable a user to adjust one or more imaging parameters affecting the digital signal during the fluoroscopy imaging operation. The control circuitry is adapted to set at least one of a range of the configurable adjustment, a step size of the configurable adjustment, or a default value of the configurable adjustment based on input from the user via the user interface.

25 Claims, 5 Drawing Sheets

FLUOROSCOPY SYSTEMS AND METHODS

BACKGROUND OF THE INVENTION

The subject matter disclosed herein relates to X-ray imaging systems and more particularly to fluoroscopy imaging systems and methods.

Fluoroscopy imaging systems facilitate the acquisition of X-ray images of a patient's anatomy (or the internal features of any animate or inanimate subject) that may be viewed as a video during an imaging operation. Such fluoroscopy systems are utilized in various applications for viewing of patient anatomy during a variety of diverse medical procedures, such as angiographic procedures, gastrointestinal procedures, cardiology procedures, and so forth. Depending on the clinical application, a radiologist typically selects an operating mode that affects multiple system parameters involved in the setup of the imaging system. For example, the selected mode may affect the X-ray dose to which the patient is exposed, the image quality obtained on the display, and so forth.

Since the various procedures in which such fluoroscopy imaging systems may be employed are diverse, the imaging parameters preset by the system to a fixed value may not be optimal for the imaging operation being performed. Additionally, an imaging parameter value suitable for one portion of an imaging operation may not be suitable for another portion of the same operation. Some traditional systems allow for operator adjustments during the imaging operation by providing a given fixed range and step size for each of the controls disposed on a control panel of the system. However, the preset range and step size, which remain the same for all operators and procedures, still limit the operator's ability to control the imaging parameters during the imaging operation. Accordingly, there exists a need for improved fluoroscopy systems that overcome such drawbacks.

BRIEF DESCRIPTION OF THE INVENTION

In accordance with one embodiment, a fluoroscopy imaging system includes an X-ray generator disposed on a first side of a subject and adapted to generate X-rays and to project the X-rays toward the subject. The imaging system also includes a detector disposed on a second side of the subject opposite the first side of the subject and adapted to receive the X-rays from the X-ray generator after being attenuated by the subject and to convert the attenuated X-rays into a digital signal representative of the subject features. The imaging system also includes control circuitry coupled to the detector and adapted to receive the digital signal from the detector, to process the digital signal, and to communicate the processed digital signal to a monitor for display. Additionally, the imaging system includes a user interface including at least one configurable adjustment adapted to enable a user to adjust one or more imaging parameters affecting the digital signal, wherein the control circuitry is adapted to set at least one of a range of the configurable adjustment, a step size of the configurable adjustment, or a default value of the configurable adjustment based on input from the user via the user interface.

In accordance with another embodiment, a fluoroscopy imaging system includes an X-ray source disposed on a first side of a subject and adapted to generate X-rays and an X-ray detector disposed on a second side of the subject opposite the first side of the subject and adapted to receive the X-rays after being attenuated by the subject and to convert the received X-rays into digital data representative of the subject features. The imaging system also includes control circuitry coupled to the X-ray source and the X-ray detector and adapted to receive the digital data from the detector, to process the digital data to produce an image of the subject features, and to control one or more imaging parameters of the X-ray source, the X-ray detector, and/or the digital data. The imaging system also includes a user interface including at least one adjustable control adapted to enable adjustment of a level of at least one of the one or more imaging parameters of the X-ray source, the X-ray detector, or the digital data, wherein a range of the adjustable control is configurable.

In accordance with a further embodiment, a method of controlling a fluoroscopy imaging system includes the steps of detecting selection of a current imaging mode of operation for the imaging operation, setting the functionality of at least one configurable adjustment disposed on a user interface of the imaging system based on the selected current imaging mode, and enabling a user to set a range of the at least one configurable adjustment.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

As described in detail below, embodiments of fluoroscopy imaging systems and methods for viewing internal features of a subject of interest, such as patient anatomy during an imaging procedure with high temporal resolution are provided. Certain embodiments may include features that enable an operator to adjust one or more imaging parameters during the fluoroscopy operation via a configurable adjustment, which may be located on a control panel of the fluoroscopy system. At least one of a range of the configurable adjustment, a step size of the configurable adjustment, or a default value of the configurable adjustment may be automatically set by a controller of the imaging system. In addition, embodiments of the present invention may also enable the operator to set at least one of a range of the configurable adjustment, a step size of the configurable adjustment, or a default value of the configurable adjustment. For example, in one embodiment, the controller may automatically set the step size of the configurable adjustment to approximately 10% and the range of the configurable adjustment to between 0% and 100%. That is, as compared to traditional systems in which the range, step size, and default value are predefined and fixed without operator input, embodiments of the present invention may automatically determine suitable values appropriate for the given operation while the operation is being performed and/or may provide the operator with the capability of altering such values as appropriate for the given operation while the operation is being performed. For example, in some traditional applications, a radiologist may transition between different procedures for which different ranges, step sizes, and/or default values may be desirable. In such applications, automatically altering such parameters during the fluoroscopy operation and/or enabling the radiologist to dynamically alter such parameters during the fluoroscopy operation may provide the operator with increased flexibility, thus enabling the operator to better optimize the acquired images.

The embodiments disclosed herein are described in the context of a general fluoroscopy imaging system in which a patient is imaged with X-rays during an imaging procedure to produce a substantially continuous flow of imaging sequences (e.g., 30 frames per second) that are displayed to an operator. However, embodiments of the present invention may be utilized in any suitable fluoroscopy system, such as recorded fluoroscopy systems for barium swallow examinations, unrecorded fluoroscopy systems for positioning procedures (e.g., advancing catheters during angiographic procedures), combination recorded and unrecorded fluoroscopy systems (e.g., gastrointestinal fluoroscopy with unrecorded fluoroscopy for diagnosis and recorded fluoroscopy for documentation), and so forth. Indeed, embodiments of the configurable adjustment and methods of controlling the configurable adjustment may be applicable in any suitable radiography or fluoroscopy system, not limited to unrecorded fluoroscopy.

Figure 1:
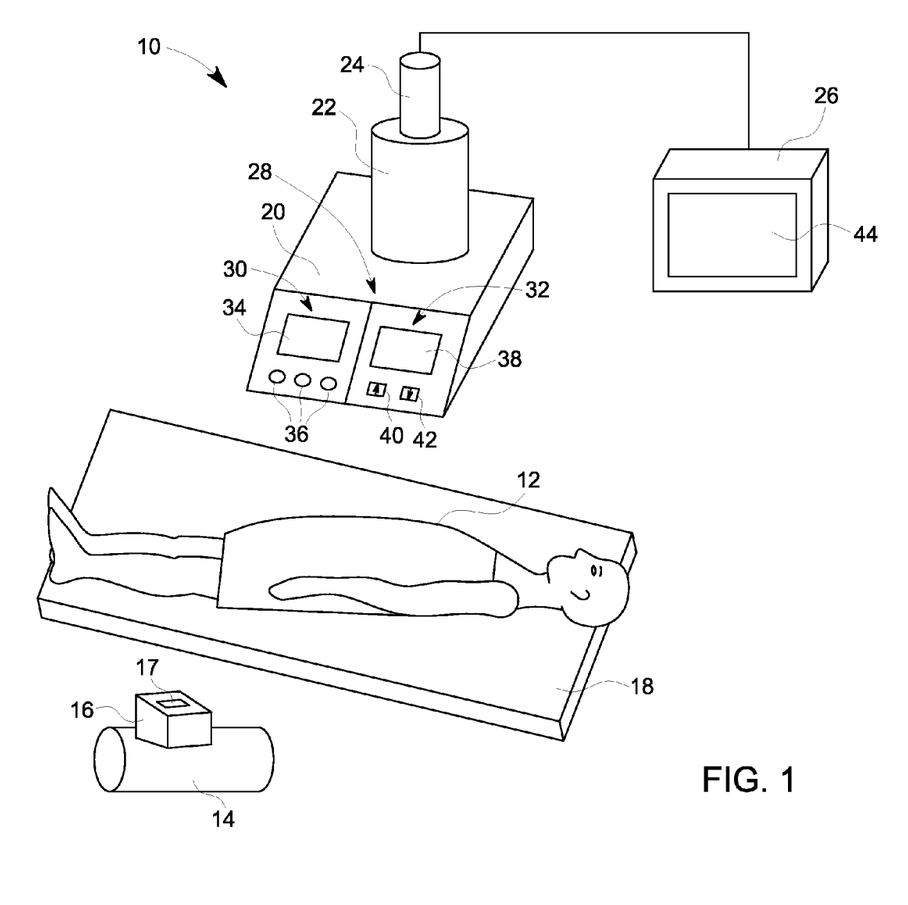
FIG. 1 illustrates an exemplary fluoroscopy system configured to continuously image the anatomy of a patient throughout an imaging operation.

Turning now to the drawings, FIG. 1 illustrates an exemplary fluoroscopy system 10 configured to continuously image the internal features of a subject, such as anatomy of a human subject or patient 12 in a medical or screening context, throughout an imaging operation. The illustrated fluoroscopy system 10 includes an X-ray tube 14 with a collimator 16, a port 17, and filters (not shown), a table 18 on which the patient is positioned, an imaging console 20, an image intensifier 22, a camera 24, and a monitor 26. The imaging console 20 includes a user interface 28 including a first control panel 30 and a second control panel 32. The first control panel 30 includes a display 34 and a plurality of configurable adjustments 36. The second control panel 32 includes a display 38 and configurable adjustments 40 and 42, which are configured to increase or decrease a parameter value, respectively. The monitor 26 also includes a display 44 configured to display a sequence of images to an operator during the imaging operation.

During operation, the X-ray source 14 generates an X-ray beam, for example, via a conventional cathode and anode X-ray production system. In some embodiments, the X-ray beam may be filtered to provide the desired energy spectrum before reaching the collimator 16. To that end, some embodiments may include one or more desired filters such as energy based filters (e.g., aluminum), equalization filters (e.g., trough filters, bow-tie filters, wedge filters, etc.), and so forth. Further, the size and shape of the X-ray beam is adjusted by the collimator 16 before emerging from the port 17. After emerging from the port 17, the X-ray beam passes through the table 18 and the patient 12 positioned thereon.

The X-ray beam is attenuated by the patient's anatomy, and at least a portion of the attenuated beam is detected by a high sensitive detector of the image intensifier 22 mounted to the imaging console 20. The image intensifier 22 is adapted to produce a projection image of an acceptable quality from a low number of X-ray photons. Such a feature may be advantageous in fluoroscopy systems since continuous imaging throughout the imaging operation may expose the patient to substantial quantities of X-ray energy. The output signals from the image intensifier 22 are continuously transferred via the video camera 24 to the monitor 26 for viewing on the display 44 during the imaging operation.

It should be noted that, while the present disclosure refers to the use of the fluoroscopy system in a medical diagnostic context, the system may be used in different contexts as well. For example, with human subjects, the system may be used for screening and similar applications. In other environments, the system may be used for detection of items in parcels, luggage, transport vehicles, and so forth. Still further, in some embodiments, such fluoroscopy imaging systems may be utilized for inspection of industrial parts, such as pipes or wind blades.

During use, as the fluoroscopy imaging operation is occurring, the operator may utilize one or more of the configurable adjustments 36, 40, and 42 to dynamically adjust one or more parameters of the imaging operation. Further, the system controller may automatically adjust and/or the operator may adjust one or more of a range, a step size, and a default value of each of the configurable adjustments throughout the fluoroscopy operation. For example, in one embodiment, the configurable adjustments 36 may be adapted to allow an operator to control at least one of a noise reduction level, a contrast level in the displayed video, a brightness of the displayed video, edge enhancement in the displayed images, and so forth. For further example, a single configurable adjustment provided for the operator to adjust the contrast level may be automatically configurable by a controller and/or configurable by the operator to determine the range, step size, and default value associated with that configurable adjustment. As such, the system may automatically alter and/or the operator may alter the range, step size, and default value of the contrast level adjustment during the imaging procedure as desired. Such a feature may offer distinct advantages over systems in which such values are predetermined during system setup and remain fixed throughout the imaging operation. For instance, by enabling the automatic and/or manual configurability of the adjustments, embodiments of the present invention may facilitate the dynamic adjustment and optimization of the video displayed on the monitor 26 during the imaging operation.

Further, it should be noted that in some embodiments, the functionality of the configurable adjustments 36, 40, and 42 may be determined prior to and/or during the imaging operation. Further, the functionality of such adjustments may be dynamically adjustable and, thus, adapted to change during the operation automatically and/or upon input from the operator. For example, in the illustrated embodiment, the user may utilize the adjustments 40 and 42 to increase and/or decrease image contrast during a first portion of the imaging operation and may further utilize the same adjustments 40 and 42 to increase and/or decrease image brightness during a second portion of the imaging operation. As such, the display 38 may be adapted to display the parameter that the configurable adjustments 40 and 42 are configured to adjust at any given time during the imaging operation.

The illustrated configurable adjustments include knobs 36 and buttons 40 and 42. However, it should be noted that in other embodiments, the configurable adjustments may include but are not limited to knobs, buttons, switches, panels, and so forth. Indeed, the configurable adjustments may be any suitable device coupled to any part of the fluoroscopy system in which at least one of the functionality, the step size, the range, and the default value may be set by an operator before or during the imaging operation. Further, in some embodiments, the configurable adjustments may not be associated with a display (e.g., 34 or 38) and may not be located on a control panel of the console 20.

It should be noted that the fluoroscopy system of FIG. 1 is described for use as a continuous fluoroscopy system configured to continuously generate an X-ray beam, for example between approximately 0.5 and 5 mA. In such systems, the video camera 24 may be configured to display the generated projection images at any suitable rate (e.g., approximately 30 frames/second). However, it should be noted that the fluoroscopy system may be any desired type of fluoroscopy system, such as a high dose rate fluoroscopy system (e.g., specially activated fluoroscopy), pulsed fluoroscopy (e.g., variable frame rate pulsed fluoroscopy), and so forth. Indeed, the configurable adjustments of the fluoroscopy system of FIG. 1 may be utilized in any suitable fluoroscopy imaging system.

Figure 2:
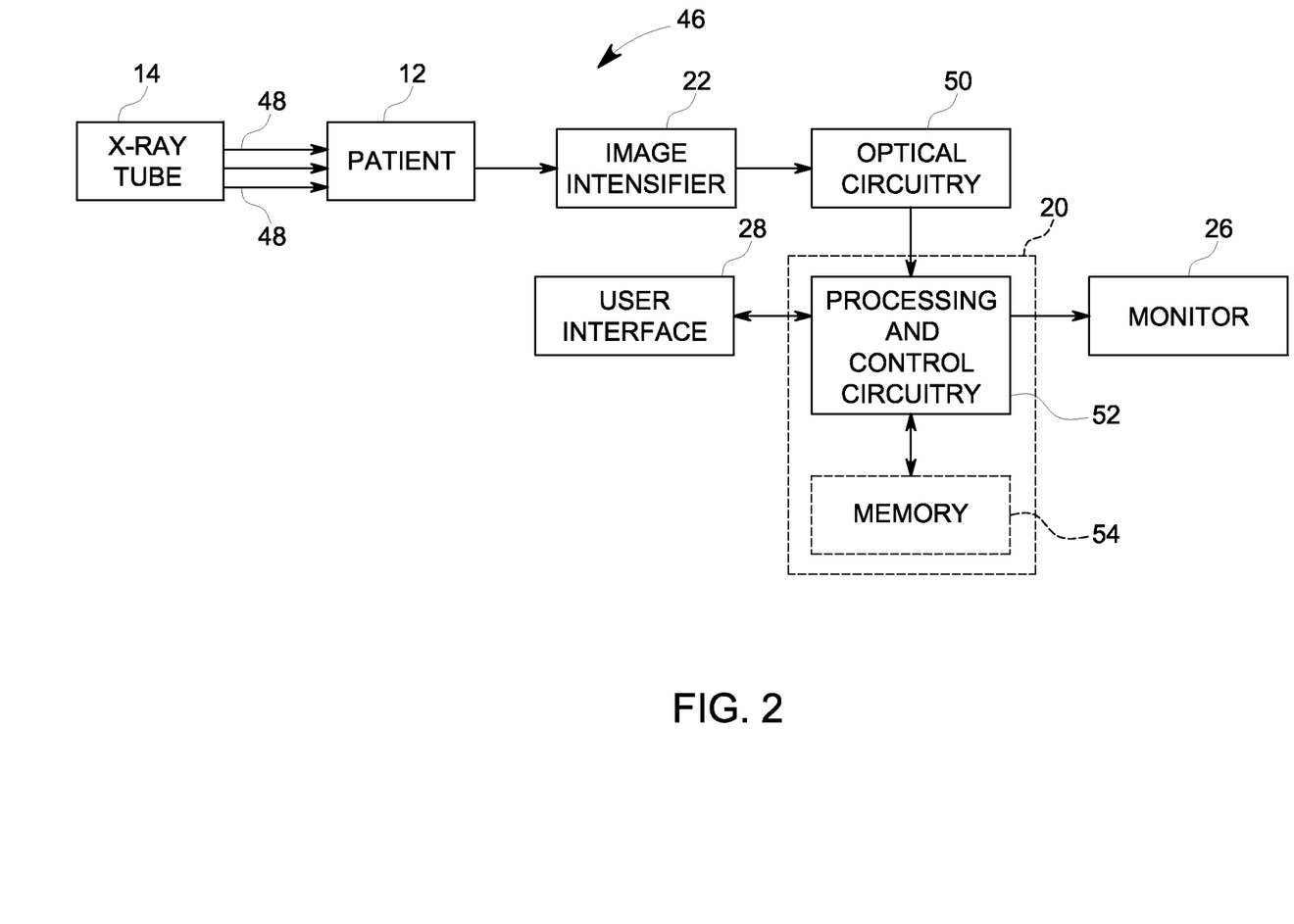
FIG. 2 is a block diagram illustrating exemplary components of a fluoroscopy system that may be operated.

FIG. 2 is a block diagram illustrating exemplary components of a fluoroscopy system 46 that may be operated in accordance with embodiments of the present invention. The illustrated fluoroscopy system 46 includes the X-ray tube 14, X-rays 48, the patient 12, the image intensifier 22, optical circuitry 50, the console 20, the user interface 28, and the monitor 26. The console 20 includes processing and control circuitry 52 and memory 54. During operation, the X-ray tube 14 generates X-rays 48 that are directed toward the patient 12. After passing through the patient, at least a portion of the attenuated X-rays are detected by the image intensifier 22, which is configured for continuous or semi-continuous operation. After detection, the image signals are transferred to the optical circuitry 50 and the processing and control circuitry 52.

The processing circuitry 52 receives the incoming signals and processes such signals for display on the monitor 26 and/or for storage in memory 54. For example, in one embodiment, the processing circuitry 52 may process the incoming signals according to one or more inputs received from the operator via the user interface. For further example, the operator may set a functionality, default value, range, and/or step size of a configurable adjustment on the user interface 28 and, subsequently, utilize the configured adjustment to communicate a desired parameter (e.g., a contrast or brightness level) to the processing circuitry 52. As such, the processing circuitry 52 is configured to receive inputs from the user interface 28 regarding one or more desired features of the configurable adjustments and to configure the adjustments disposed thereon according to the received inputs. Additionally, the processing circuitry 52 is further adapted to utilize inputs received from the configured adjustments to process the received image signals before displaying such signals on the monitor 26. Still further, depending on the current operational mode, the control circuitry 52 may store one or more of the received signals to the memory 54. For instance, in certain angiographic procedures, during catheter positioning in the patient 12, the processing circuitry 52 may be adapted to display the received image signals on the monitor 26. However, after proper placement of the catheter has been established, the processing circuitry 52 may be adapted to record and store pulsed radiography images as radiographic contrast media is injected into the vessels or body cavity of interest. In such a way, the processing circuitry 52 may operate the imaging system 46 to alternate between recorded and unrecorded fluoroscopy if desired for the given operation.

Figure 3:
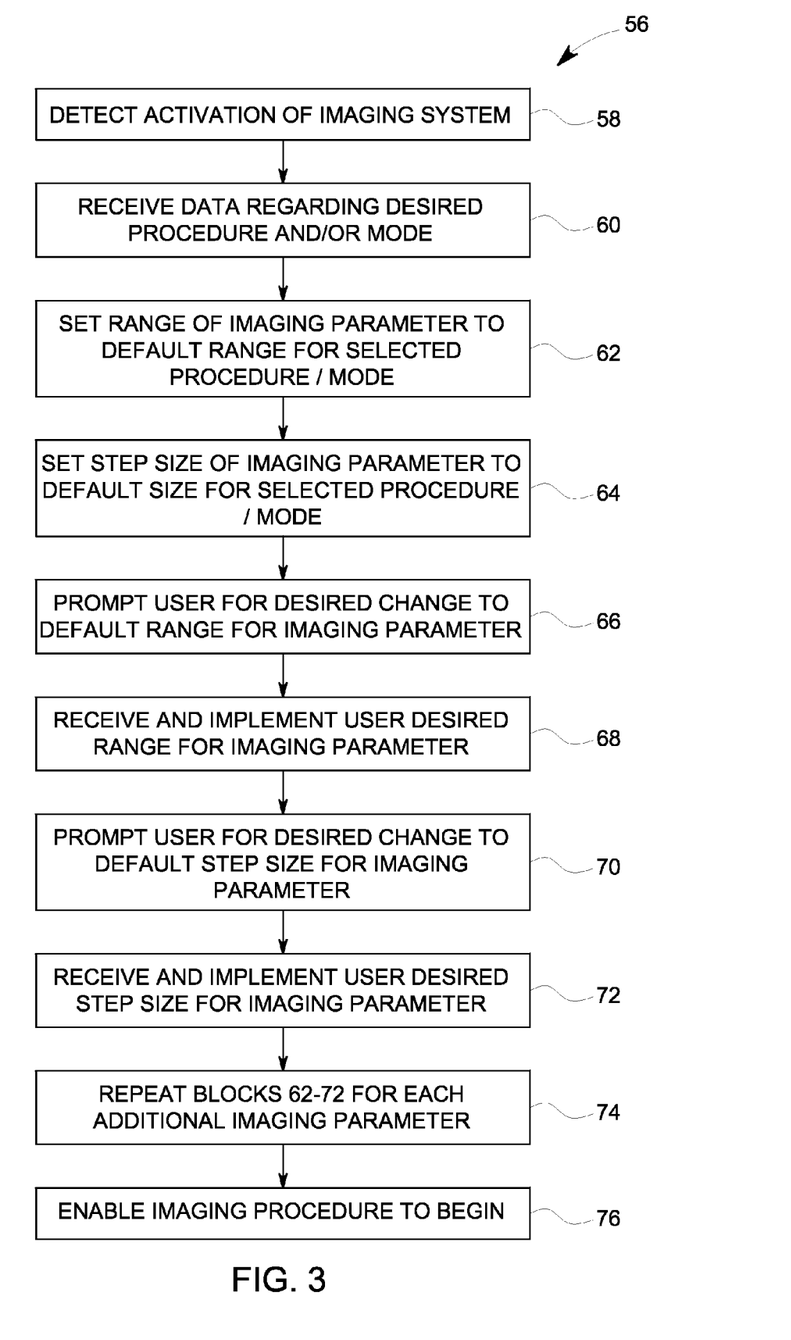
FIG. 3 illustrates an exemplary method that may be employed by the control circuitry of FIG. 2 to operate a fluoroscopy system.

FIG. 3 illustrates an exemplary method 56 that may be employed by the control circuitry of FIG. 2 to operate a fluoroscopy system in accordance with embodiments of the present invention. The method 56 includes detecting activation of the imaging system (block 58), for example, when the fluoroscopy system is powered ON by the operator. After system activation, the control circuitry receives data regarding a desired procedure and/or mode (block 60). For instance, an operator may specify a pediatric mode, an adult mode, a contrast material type (e.g., barium, iodine, etc.), a type of surgical instrument being utilized (e.g., syringe, metal instrument, etc.), an imaging frame rate, and so forth. That is, the controller may be configured to operate according to the selected mode or procedure type.

The method 56 also includes setting a range of a configurable adjustment associated with an imaging parameter to a default range for the selected procedure and/or mode (block 62). Similarly, the method 56 includes setting a step size of the configurable adjustment associated with the imaging parameter to a default step size for the selected procedure or mode (block 64). It should be noted that the default settings for the range and step size may be automatically determined by the controller independent of operator input or may be set by the controller based on operator instructions for the particular mode or procedure selected. In such a way, the default settings for the configurable adjustments may be altered automatically and/or based on operator input if desired for the given application.

Once initialized, the control circuitry is configured to prompt the operator for a desired change to the default range for the imaging parameter the configurable adjustment controls (block 66) and to implement the range desired by the operator (block 68). For example, in an embodiment in which a pediatric patient is being imaged, the operator may restrict the range of the configurable adjustment for the imaging parameter to a lower range (e.g., 0-2 range) rather than a higher range (e.g., 0-9 range) suitable for an adult patient. Alternatively, in another embodiment, the control circuitry may be configured to automatically determine and implement a suitable range for the imaging parameter of the configurable adjustment controls based on the current exam type and incoming image data. Such a feature may offer advantages over systems that automatically determine and set a range based solely on a procedure type since in some instances, based on the size of the patient, a variety of different ranges may be desired for the same procedure type.

The method 56 also includes prompting the operator for a desired change to the default step size initiated for the configurable adjustment at setup (block 70) and implementing the step size desired by the operator (block 72). For example, the user may adjust the step size of the configurable adjustment associated with an imaging parameter to the desired step size appropriate for fine tuning of the specified range. In such a way, the controller may configure the range and step size of the configurable adjustment for the first imaging parameter as desired by the operator. Further, the same logic may be utilized to set the range and step size of any additional configurable adjustments configured to control additional imaging parameters (block 74), and the imaging procedure may be enabled (block 76). It should be noted that although the illustrated method 56 is described in the context of the startup of the fluoroscopy system, in other embodiments, such logic may be utilized throughout the imaging operation to adjust the range and step size as desired.

Figure 4:
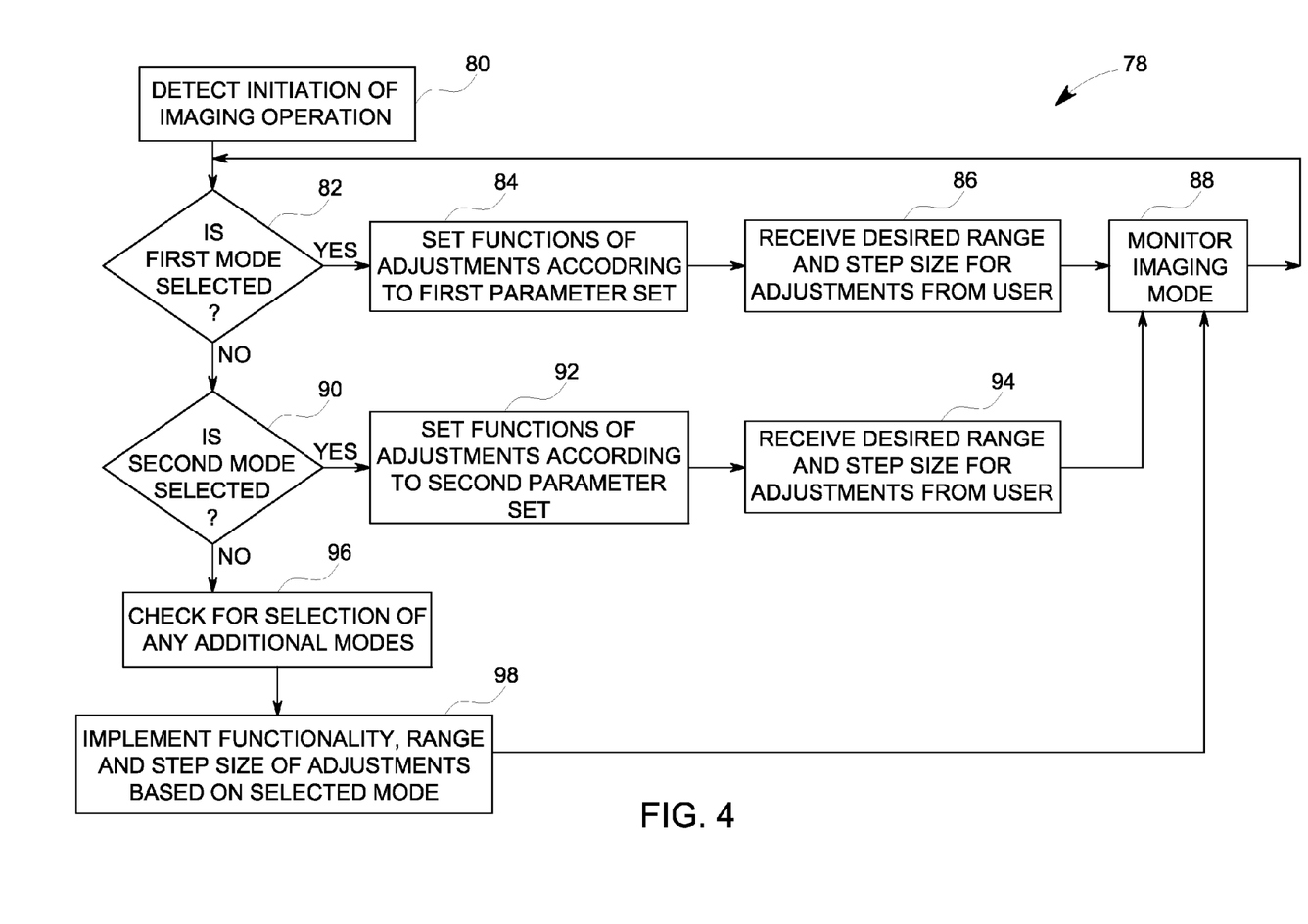
FIG. 4 is a block diagram illustrating an exemplary method that may be utilized by the controller to set the functionality of the configurable adjustments based on a user selected mode.

FIG. 4 is a block diagram illustrating an exemplary method 78 that may be utilized by the controller to set the functionality of the configurable adjustments based on a user selected mode in accordance with embodiments of the present invention. Specifically, the method 78 includes detecting initiation of a fluoroscopy imaging operation (block 80) and checking whether a first mode is selected (block 82). For example, the control circuitry may check for selection of a pediatric mode, an adult mode, a contrast material mode, and so forth. If the first mode is selected, the controller is configured to set the functions of the configurable adjustments according to a first parameter set (block 84). That is, the controller may assign a parameter for each of the configurable adjustments to control based on the selected mode. For example, a first configurable adjustment may be associated with contrast level, a second configurable adjustment may be associated with brightness level, and so forth.

After setting the functionality of the configurable adjustments according to the first selected mode, the controller is further configured to receive a desired range and step size for each of the configurable adjustments from the operator or automatically from the system controller (block 86). That is, as before, the user may define a desired range and step size based on the imaging mode, patient size, and so forth. Throughout subsequent operation of the imaging system, the controller continues to monitor the selected imaging mode (block 88) and, if a change in imaging mode occurs, the controller may reset one or more of the functions of the configurable adjustments.

When the first imaging mode is not selected, the controller checks whether a second mode is selected (block 90) and, if so, the controller set the functions of the configurable adjustments according to a second parameter set (block 92). For example, the second mode may be an adult imaging mode, and the controller may set the functionalities of the adjustments accordingly. As before, the controller then receives a desired range and step size for each of the configurable adjustments that have been configured to set an appropriate imaging parameter (block 94) and continues to monitor the imaging operation for changes to the selected mode (block 88).

If the second mode is not selected, the controller checks for selection of any additional modes associated with the given imaging system (block 96) and implements a functionality, step size, and range for each of the configurable adjustments based on the selected mode and operator inputs (block 98). That is, it should be noted that although only two mode checks are illustrated, in additional embodiments, any desired number of mode checks and functional parameter sets may be included in the control logic. In such a way, certain embodiments of the control circuitry disclosed herein may be configured to set a functionality of the configurable adjustments based on a selected imaging mode.

Figure 5:
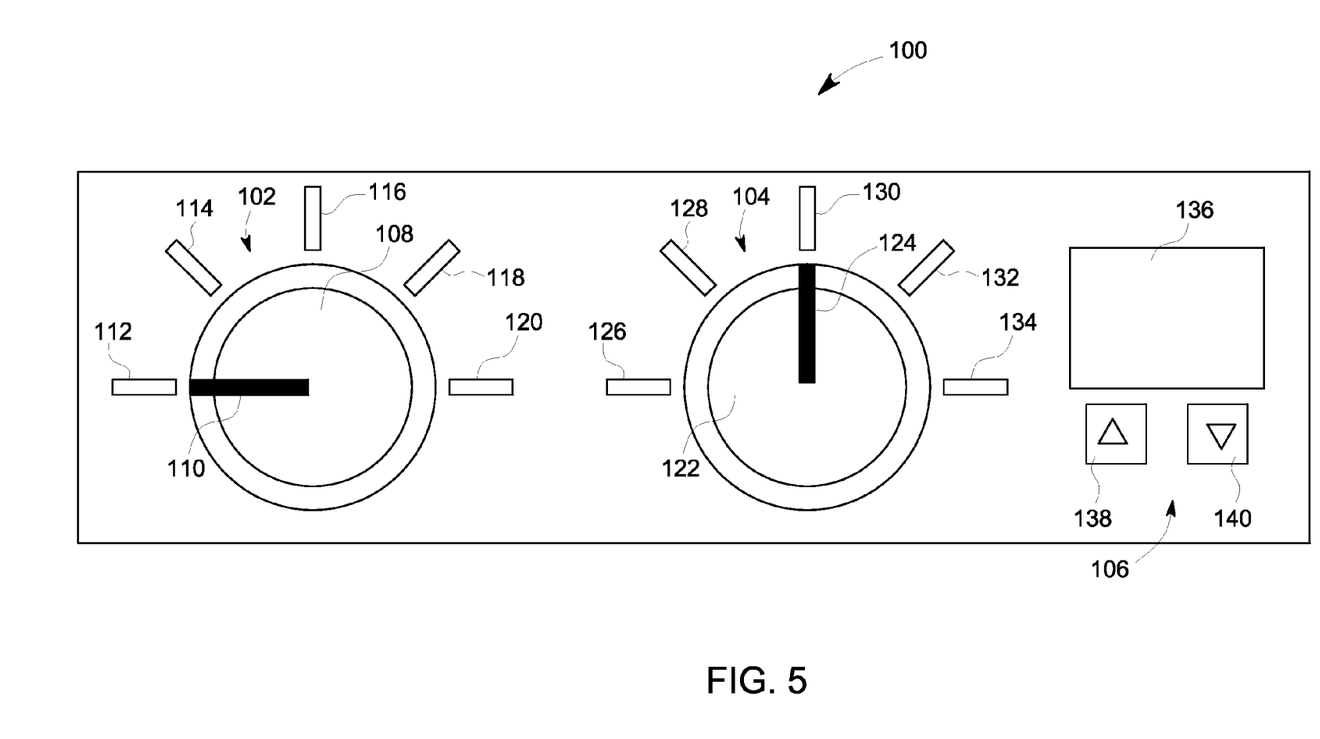
FIG. 5 illustrates an embodiment of a control panel including one or more exemplary configurable adjustments.

FIG. 5 illustrates an embodiment of a control panel 100 including one or more exemplary configurable adjustments in accordance with aspects of the present invention. The control panel 100 includes a first configurable adjustment panel 102, a second configurable adjustment panel 104, and a third configurable adjustment panel 106. The first panel 102 includes a knob 108 having an indicator 110 that may be directed toward one or more increment markers 112, 114, 116, 118, and 120. The second panel 104 includes a second knob having a second indicator 124 that may be directed toward one ore more increment markers 126, 128, 130, 132, and 134. Further, the third panel 106 includes a display 136, an increase button 138, and a decrease button 140.

During operation, functions are assigned to the first knob 108 and the second knob 122, for example, directly as specified by an operator or indirectly via determination by the controller based on an operator selected mode. Similarly, a function of the third panel 106 may be determined, and the parameter the buttons 138 and 140 are configured to adjust may be shown on the display 136. A step size may also be assigned to each of the knobs 108 and 122. That is, the amount by which the imaging parameter is increased or decreased when the knobs are rotated between increment markers (e.g., between marker 112 and marker 114 or between marker 130 and marker 132) may be set by an operator. Additionally, a range may be assigned to each of the knobs 108 and 122. That is, the amount of change allowed for the given imaging parameter as the knobs are moved from the extreme left position (e.g., marker 112 or marker 126) to the extreme right position (e.g., marker 120 or marker 134) may also be set by the operator.

Similarly, a range and a step size for the third panel 106 may be set by the controller based on operator input. For instance, the amount by which the buttons 138 and 140 will increase or decrease the imaging parameter upon each depression (i.e., the step size) may be set by the operator. Further, it should be noted that once set, the ranges and step sizes of the configurable adjustments disposed on panels 102, 104, and 106 may be readjusted by the operator throughout the imaging operation. Still further, the configurable adjustments shown on the illustrated control panel 100 are embodiments of suitable configurable adjustments and are not meant to limit the invention to knobs and buttons. Any suitable adjustment configurable with regard to at least one of a default value, range, step size, or functionality may be utilized in accordance with embodiments of the present invention.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A fluoroscopy imaging system, comprising:
an X-ray generator disposed on a first side of a subject and configured to generate X-rays and to project the X-rays toward the subject;
a detector disposed on a second side of the subject opposite the first side of the subject and configured to receive the X-rays from the X-ray generator after being attenuated by the subject and to convert the attenuated X-rays into a digital signal representative of the subject features;
control circuitry coupled to the detector and configured to receive the digital signal from the detector, to process the digital signal, to communicate the processed digital signal to a monitor for display during a fluoroscopy imaging operation; and
a user interface comprising at least one configurable adjustment configured to enable a user to adjust one or more imaging parameters affecting the digital signal during the fluoroscopy imaging operation, wherein the control circuitry is configured to set at least a range of the configurable adjustment and to determine and set a step size of the configurable adjustment to a portion of the range.

2. The imaging system of claim 1, wherein the control circuitry is further configured to set a functionality of the configurable adjustment based on input from the user via the user interface.

3. The imaging system of claim 1, wherein the configurable adjustment is configured to adjust at least one of a noise level, an image contrast level, an agent enhancement level, and a brightness level.

4. The imaging system of claim 1, wherein the control circuitry is further configured to receive a selected mode via the user interface and to set the functionality of the configurable adjustment based on the selected mode.

5. The imaging system of claim 1, wherein the configurable adjustment is at least one of a knob, a depressible button, and an electronic interface.

6. The imaging system of claim 1, wherein at least one of the type, range, step size, or default value of the configurable adjustment is set based on at least one of input from the user via the user interface and an automatic determination of the control circuitry.

7. The imaging system of claim 1, wherein the control circuitry is configured to alert a user when one or more of the type, range, and step size of the configurable adjustment is altered from a default value.

8. The imaging system of claim 4, wherein the selected mode is at least one of a pediatric mode, a contrast agent mode, and a surgical instrument mode.

9. A fluoroscopy imaging system, comprising:
an X-ray source disposed on a first side of a subject and configured to generate X-rays;
an X-ray detector disposed on a second side of the subject opposite the first side of the subject and configured to receive the X-rays after being attenuated by the subject and to convert the received X-rays into digital data representative of the subject features;
control circuitry coupled to the X-ray source and the X-ray detector and configured to receive the digital data from the detector, to process the digital data to produce an image of the subject features, and to control one or more imaging parameters of the X-ray source, the X-ray detector, and/or the digital data; and
a user interface comprising at least one adjustable control configured to enable adjustment of a level of at least one of the one or more imaging parameters of the X-ray source, the X-ray detector, or the digital data during a fluoroscopy imaging operation, wherein a range of the adjustable control is configurable;
wherein the control circuitry is configured to dynamically adjust a step size of the adjustable control to a preset portion of the range during an imaging operation as the range of the adjustable control is adjusted.

10. The imaging system of claim 9, wherein the one or more imaging parameters comprise at least one of a noise level, an image contrast level, an agent enhancement level, an X-ray intensity level, a detector sensitivity level, and a brightness level.

11. The imaging system of claim 9, wherein a step size of the adjustable control is configured to be set by the operator and communicated to the control circuitry via the user interface.

12. The imaging system of claim 9, wherein the functionality of the adjustable control is configured to be determined by the control circuitry based on an imaging mode or procedure indicated by the operator via the user interface.

13. The imaging system of claim 9, wherein the range of the adjustable control is configured to be set by an operator and communicated to the control circuitry via the user interface.

14. The imaging system of claim 9, wherein the adjustable control is at least one of a knob, a depressible button, and an electronic interface.

15. The imaging system of claim 9, wherein the control circuitry is configured to alert a user when alone or more of the type, range, or step size of the configurable adjustment is altered from a default value based on input from the user via the user interface or a determination automatically performed by the control circuitry.

16. A method of controlling a fluoroscopy imaging system, comprising:
detecting selection of a current imaging mode of operation for the imaging operation;
setting the functionality of at least one configurable adjustment disposed on a user interface of the imaging system based on the selected current imaging mode;
enabling a user to set a range of the at least one configurable adjustment during the fluoroscopy imaging operation; and
enabling a user to set a step size of the at least one configurable adjustment.

17. The method of claim 16, further comprising the step of detecting a change in the current imaging mode of operation during the imaging operation and resetting the functionality of the at least one configurable adjustment based on the detected current imaging mode of operation.

18. The method of claim 16, further comprising the step of enabling the user to reset the range of the at least one configurable adjustment after the functionality of the at least one configurable adjustment has been reset.

19. The method of claim 18 further comprising the step of enabling the user to reset a step size of the at least one configurable adjustment after the functionality and range of the at least one configurable adjustment has been reset.

20. The method of claim 16, further comprising the step of automatically determining one or more of a suitable range and a suitable step size of the configurable adjustment based on image data obtained during an imaging operation.

21. The method of claim 16, further comprising the step of alerting the user when one or more of the type, range, or step size of the configurable adjustment is altered from a default value based on input from the user or an automatic determination.

22. A method of controlling a fluoroscopy imaging system, comprising:
detecting selection of a current imaging mode of operation for the imaging operation;
setting the functionality of at least one configurable adjustment disposed on a user interface of the imaging system based on the selected current imaging mode;
enabling a user to set a range of the at least one configurable adjustment during the fluoroscopy imaging operation; and
automatically determining and setting a step size of the at least one configurable adjustment based on the selected range.

23. The method of claim 22, further comprising the step of detecting a change in the current imaging mode of operation during the imaging operation and resetting the functionality of the at least one configurable adjustment based on the detected current imaging mode of operation.

24. The method of claim 22, further comprising the step of automatically determining one or more of a suitable range and a suitable step size of the configurable adjustment based on image data obtained during an imaging operation.

25. The method of claim 22, further comprising the step of alerting the user when one or more of the type, range, or step size of the configurable adjustment is altered from a default value based on input from the user or an automatic determination.

* * * * *